(12) United States Patent
Gauthier et al.

(10) Patent No.: US 8,087,307 B2
(45) Date of Patent: Jan. 3, 2012

(54) REMOVAL OF PARTICULATES FROM GAS SAMPLING STREAM

(75) Inventors: Philippe Jean Gauthier, Fullerton, CA (US); Neil Colin Widmer, San Clemente, CA (US)

(73) Assignee: General Electric Company, Schenectady, NY (US)

( * ) Notice: Subject to any disclaimer, the term of this patent is extended or adjusted under 35 U.S.C. 154(b) by 439 days.

(21) Appl. No.: 12/368,347

(22) Filed: Feb. 10, 2009

(65) Prior Publication Data
US 2010/0199786 A1      Aug. 12, 2010

(51) Int. Cl.
*G01N 1/22* (2006.01)

(52) U.S. Cl. .................. 73/863.23; 73/863.41

(58) Field of Classification Search .............. 73/863.21, 73/863.41, 863.51, 863.57
See application file for complete search history.

(56) References Cited

U.S. PATENT DOCUMENTS

| | | | |
|---|---|---|---|
| 3,961,896 A * | 6/1976 | Dunn | 436/173 |
| 4,161,883 A | 7/1979 | Laird et al. | |
| 4,286,472 A * | 9/1981 | Pocock | 73/863.24 |
| 4,653,334 A * | 3/1987 | Capone | 73/863.81 |
| 4,856,352 A | 8/1989 | Daum et al. | |
| 5,824,919 A * | 10/1998 | Hansen | 73/863.23 |
| 6,869,800 B2 * | 3/2005 | Torgerson et al. | 436/37 |
| 7,337,683 B2 | 3/2008 | DeFriez et al. | |
| 7,523,680 B2 * | 4/2009 | Zimmer et al. | 73/863.23 |

FOREIGN PATENT DOCUMENTS

| | | | |
|---|---|---|---|
| EP | 244936 | * 11/1987 | 73/863.23 |
| GB | 1443465 A | 7/1976 | |
| JP | 2000227389 A | 8/2000 | |
| SU | 455263 A1 | 12/1974 | |

OTHER PUBLICATIONS

EP 10152743.0. European Search Report and Written Opinion, Jul. 14, 2010.
Abstract of Soviet Patent SU 455263, Apr. 21, 1975, 1 page.

* cited by examiner

*Primary Examiner* — Daniel Larkin
(74) *Attorney, Agent, or Firm* — Cantor Colburn LLP

(57) ABSTRACT

A sample probe includes a sample probe tip filter and a deflector disposed in relation to the sample probe tip filter, where the deflector is operable to deflect particles in a gas stream away from the sample probe tip filter.

18 Claims, 3 Drawing Sheets

REMOVAL OF PARTICULATES FROM GAS SAMPLING STREAM

BACKGROUND OF THE INVENTION

The subject matter disclosed herein relates to gas stream sampling and, in particular, to reducing the number of particulates from entering a sample probe at the sampling location of a gas stream.

Fly ash is one of several pollutant particulate residues generated in the combustion of coal or other fossil fuels by, e.g., boilers or furnaces. Fly ash is generally captured from the chimneys of coal-fired power plants. In the past, fly ash was generally released into the atmosphere, but pollution control equipment mandated in recent decades now requires that the fly ash be captured instead of being released into the environment. In the U.S., the fly ash is now generally collected and stored at the power plant. Depending upon the source and makeup of the coal being burned, the components of the fly ash produced vary considerably, but fly ash typically includes substantial amounts of silicon dioxide ($SiO_2$) (both amorphous and crystalline) and calcium oxide (CaO). Fly ash is commonly used to supplement cement in concrete production, where it can bring both technological and economic benefits, and is increasingly finding use in the synthesis of geopolymers and zeolites.

However, when sampling a gas stream, for example, in a combustion furnace or boiler operating at relatively high temperatures (e.g., 900° F.-1500° F.), it is generally difficult to continuously separate on-line or in-situ the relatively hot fly ash from the sampling flue gas such that primarily the flue gas is sensed. Removal of fly ash in a relatively substantial amount from the gas sampling stream at or near the sample probe or sensor is needed for typical sampling applications. Failure to reduce the amount of fly ash leads to: 1) ash accumulation within the sampling probe, which may lead to plugging of the probe; and 2) ash accumulation on the analyzer's sensors, which may reduce or impair the sensing ability and accuracy and also the lifetime of the sensors.

There exist many techniques to remove fly ash from hot flue gas sampling streams. A common technique is to use a sampling conditioning system to cool down the temperature of the sample flue gas. The separation of fly ash from the sample flue gas stream is then performed via a filtering device such as a fabric filter, cyclone, or other filtering device system. This approach turns out to be cumbersome and expensive due to the additional parts needed. In addition, this type of system usually requires relatively high maintenance due to ash disposal requirements from the filtering system.

BRIEF DESCRIPTION OF THE INVENTION

According to one aspect of the invention, a sample probe includes a sample probe tip filter, and a deflector disposed in relation to the sample probe tip filter, where the deflector is operable to deflect particles in a gas stream away from the sample probe tip filter.

According to another aspect of the invention, a sample probe for sampling flue gas in a gas sampling stream includes a sample probe filter having a tip portion located at one end of the sample probe filter, the tip portion of the sample probe filter being operable to sample the flue gas in the gas sampling stream. The sample probe also includes a deflector disposed in relation to the sample probe filter, the deflector having a length that at least substantially covers the sample probe filter.

According to yet another aspect of the invention, an extension of a sample probe includes a deflector that connects to a support sleeve pipe, the deflector having a length that extends beyond an end of the support sleeve pipe.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Figure 1:
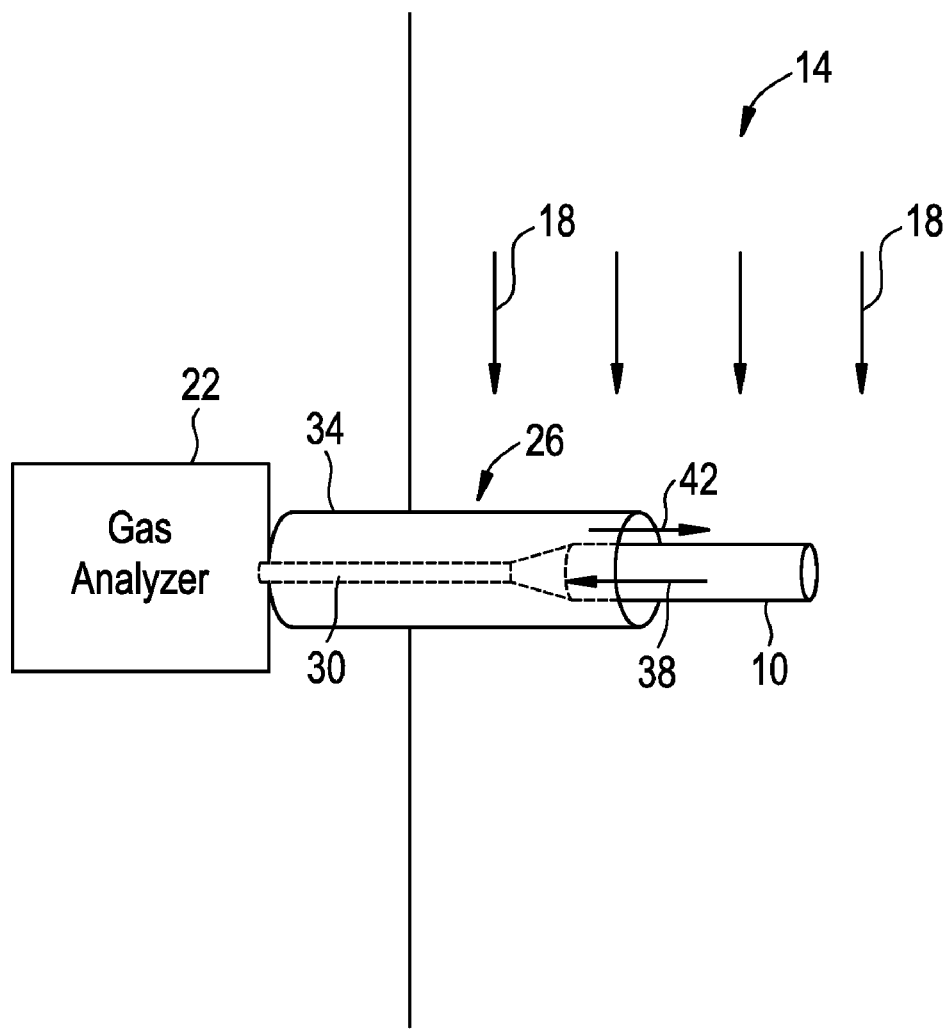
FIG. 1 illustrates an embodiment of a sample probe inserted in a flue gas stream.

In FIG. 1 is an embodiment of a sample probe filter 10 inserted in a relatively hot flue gas stream 14 within, e.g., a furnace or boiler. The high temperature flue gas (e.g., 900° F. to 1500° F.) may travel downward as indicated by the lines with arrowheads 18 in FIG. 1, and contact the sample probe filter 10 typically at a ninety-degree angle as shown, but may contact the filter 10 at other angles as well. Also, the flue gas may travel in any other direction, such as horizontally through a corresponding horizontally oriented flue gas path. The hot flue gas typically contains undesirable (e.g., pollutant) particulate matter such as fly ash. The flue gas enters the sample probe filter 10 due to a vacuum pressure created by a vacuum system associated with the gas analyzer equipment 22. The analyzer sample probe 26 also comprises at least one pipe section 30. The sample probe filter 10 is disposed within the pipe section 30 and a tip portion of the sample probe filter 10 is located at the end of the pipe section 30, with the pipe section 30 and probe tip filter 10 protruding into the flue gas stream 14. The pipe section 30 and probe tip filter 10 may be inserted within a support sleeve pipe 34, which supports the sample probe pipe section(s) 30. If more than one pipe section 30 is utilized, these sections 30 may be connected together to form one contiguous pipe section 30. The support sleeve pipe 34 is utilized to avoid bending of relatively long sample probes 26 (e.g., three to twenty feet) inside the furnace. The sample probe tip filter 10 may extend beyond the support sleeve pipe 34 by, e.g., a few inches to collect flue gas 14 from the combustion furnace. The flue gas 14 enters through the probe tip filter 10, flows through the sample probe pipe section(s) 30 as indicated by the line with the arrowhead 38 in FIG. 1, and through the sensors within the analyzer 22. The sampled flue gas is then released back into the hot combustion furnace gas stream 14 via a gas pathway indicated by the line with the arrowhead 42 in FIG. 1 and defined between the support sleeve pipe 34 and the sample probe pipe section(s) 30.

Figure 5:
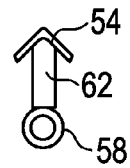

In FIGS. 2-5 taken together is a sample probe tip filter 50 with a deflector 54, which reduces the amount of fly ash particulates that impinge on the probe tip filter 50 according to an embodiment of the invention. In this embodiment, the deflector 54 may comprise a heavy gauge metal or other suitable material in the form of a shield having any number of suitable forms and shapes. For example, the deflector 54 may comprise an inverted "V"-shaped angled shield as illustrated in FIG. 5. However, the shape of the deflector may be round, flat or some other suitable shape, as desired. The deflector 54 may, in an embodiment, be added on top of and at the end of, and thus connected to, the support sleeve pipe 58 (see the side and perspective views of FIGS. 2 and 4, respectively). However, other embodiments may omit the support sleeve pipe 58, and the deflector 54 may be connected to other items, such as the analyzer 22 using appropriate means. If the support sleeve pipe 58 is included, the deflector 54 need not necessarily be connected to the support sleeve pipe 58 or may be indirectly connected to the support sleeve pipe 58 through other means. If connected to the support sleeve pipe 58, the deflector 54 may be an extension of the support sleeve pipe 58. The deflector 54 may be attached to the support sleeve pipe 58 via metal rods, a metal piece or by other suitable mechanical support devices 62 (see the side and end views of FIGS. 2 and 5, respectively). The length of the deflector 54 may, in an embodiment, be such that it substantially covers the sample probe tip filter 50, regardless of whether or not the deflector 54 is connected to the support sleeve pipe 58. The deflector 54 may be set at an elevation of, e.g., a few inches above the sample probe tip filter 50. In this configuration, the deflector 54 is disposed upstream of the sample probe tip filter 50 in the hot flue gas stream 14 (FIG. 1).

The purposes of the deflector 54 are to: 1) deflect (and, thus, reduce) a substantial amount of the fly ash particulates from directly entering into and accumulating onto the sample probe tip filter 50 (e.g., so that primarily the hot flue gas enters the sample probe tip filter 50 and ultimately the analyzer 22 for sampling thereby); and 2) prevent the high velocity flue gas from directly contacting the sample probe tip filter 50, which could damage the filter 50 over time. Typically the deflector 54 will deflect the relatively larger fly ash particles from entering the sample probe tip filter 50 and only allow the relatively smaller fly ash particulates along with the flue gas to enter the sample probe tip filter 50.

Figure 2:
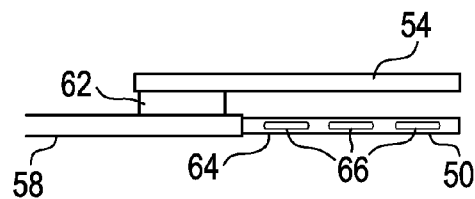
FIGS. 2-5 are various side, top, perspective and end views, respectively, that together illustrate a sample probe with a deflector in accordance with an embodiment of the invention.
Figure 3:
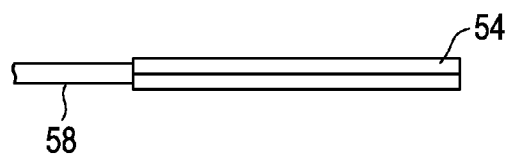
Figure 4:
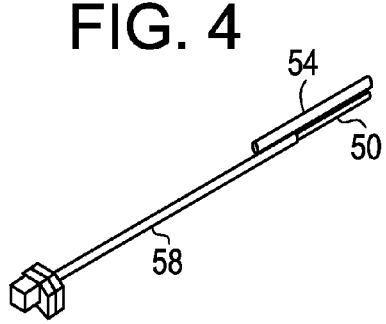

The design of the sample probe tip filter 50 may vary between applications, but in one embodiment the filter 50 may comprise a fabric filter inserted inside one or more concentric pipes 64 with open slots 66 along the lengths of the concentric pipes 64 (FIG. 2). In the alternative, the support sleeve pipe 58 may be extended to some distance over the sample probe tip filter 50 and thus have the open slots 66 or other holes or perforations formed therein. In embodiments, the sample probe tip filter openings 66 may begin at approximately six to ten inches (or any other suitable distance greater than or less than six to ten inches) past the end of the support sleeve pipe 58. The openings 66 help to avoid any analyzer exhaust sample gas from the support sleeve pipe 58 or the concentric pipes 64 from recirculating back to and into the sample probe tip filter 50. The analyzer exhaust sample gas may undesirably affect the accuracy of the sampling of the flue gas if the exhaust sample gas were to recirculate back into the analyzer 22, and the distance from the beginning of the openings 66 from the end of the support sleeve pipe 58 may be chosen as needed to avoid any such undesirable recirculation.

Figure 6:
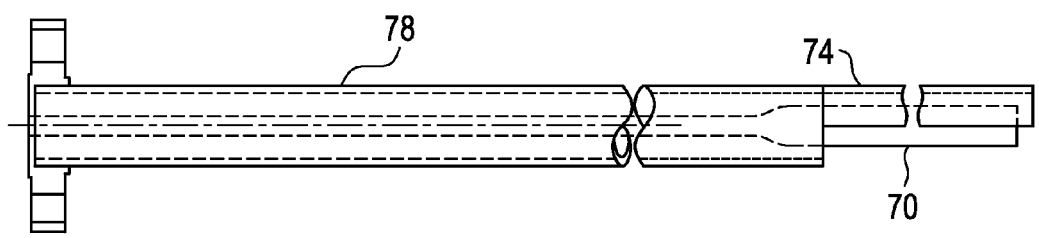
FIG. 6 illustrates a sample probe with a deflector in accordance with another embodiment of the invention.

In FIG. 6 is another embodiment of a sample probe tip filter 70 with a deflector 74 utilized again to reduce the amount of fly ash that impinges on the probe tip filter 70. This embodiment is somewhat similar to the previous embodiment of FIGS. 2-5, but instead of using a separate deflector 54, the support sleeve pipe 78 is extended by an additional half-pipe section support sleeve length 74. The half pipe section deflector 74 may be considered an extension of the support sleeve pipe 78, and its length may, in an embodiment, be such that it substantially covers the sample probe tip filter 70 extending from the support sleeve pipe 78. As with the embodiment of FIGS. 2-5, in the embodiment of FIG. 6 the half pipe section deflector 74 is disposed upstream of the sample probe tip filter 70 in the flue gas stream 14 (FIG. 1).

Figure 7:
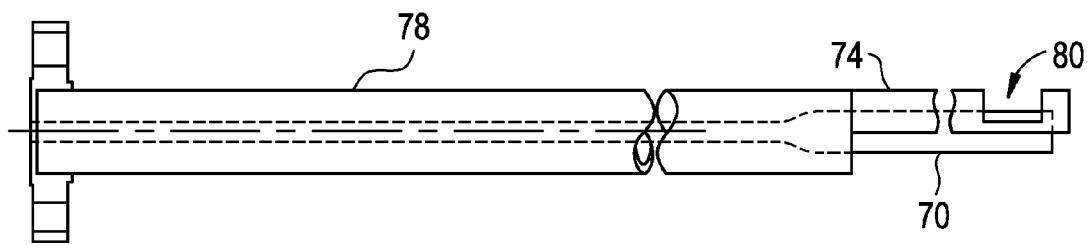
FIG. 7 is an illustration of an alternative embodiment of the sample probe shown in FIG. 6.

The purposes of the half pipe section support sleeve deflector 74 are similar to those of the deflector 54 of the embodiment of FIGS. 2-5; that is, to: 1) deflect (and, thus, reduce) a substantial amount of the fly ash particulates from directly entering into and accumulating onto the sample probe tip filter 70 (e.g., so that primarily the hot flue gas enters the sample probe tip filter 70 and ultimately the analyzer 22 for sampling thereby); and 2) prevent high velocity flue gas from directly contacting the sample probe tip filter 70, which could damage the filter 70 over time. The support sleeve 74 does not need to be a half pipe. Instead, the support sleeve may comprise some other portion of a completely enclosed pipe (e.g., a one-third section, a one-quarter section, or any other angled amount less than a full 360 degree circumferential pipe section. Alternatively, if the support sleeve pipe 78 is something other than of cylindrical shape (e.g., a square opening), then the support sleeve 74 may be a portion of that other shape or even a different shape. The design of the sample probe tip filter 70 may vary between applications, but in one embodiment may comprise a fabric filter inserted inside one or more concentric pipes with openings in the form of open slots, perforations, etc. located along the length of the concentric pipes, similar to the embodiment shown in FIG. 2. As with the embodiment of FIGS. 2-5, in the embodiment of FIG. 6 the sample probe tip filter slot openings may begin at approximately six inches (or some other suitable distance) past the end of the support sleeve pipe 78 to avoid any analyzer exhaust sample gas from the support sleeve pipe 78 to recirculate into the sample probe tip filter 70. Also, the half pipe support sleeve deflector 74 may have one or more openings formed therein for similar reasons, which is indicated by reference number 80 and is shown in FIG. 7.

Embodiments of the invention reduce the amount of hot temperature fly ash from entering into the sampling flue gas analyzer system. This allows for in-situ separation of fly ash from sample flue gas streams in hot temperature furnaces with little or no maintenance required. Embodiments of the present invention may be used to continuously sample flue gas in a hot furnace that carries high loads of fly ash or dust particulates, such as coal fired boiler units, cement kilns or other plants with relatively high particulate loads in their furnace.

Embodiments of the invention comprise filtering concepts that meet the following criteria: 1) reduce the amount of fly ash particulates that enter into the flue gas analyzer sampling system by segregating a substantial amount of the fly ash particulates from the gas sampling stream; 2) protect the sample probe tip filter from any damage that may be caused by high velocity of flue gases, proximity of soot blowers or other damaging devices, by diverting the hot flue gases away from direct contact with the sample probe filter tip; and 3) applies to hot temperature gases in the range of about 900° F. to about 1500° F. This allows embodiments of the invention to perform in-situ hot flue gas sampling in hot combustion furnaces or boilers with relatively high loads of particulates such as fly ash, thereby allowing the flue gas analyzer to be used in a broader range of environmentally harsh dust conditions.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A sample probe, comprising:
    a sample probe tip filter;
    a deflector disposed in relation to the sample probe tip filter, where the deflector is operable to deflect particles in a gas stream away from the sample probe tip filter; and
    a support sleeve pipe, a portion of the sample probe tip filter being disposed within the support sleeve pipe, and the support sleeve pipe being configured for providing support to the sample probe tip filter to substantially avoid bending of the sample probe tip filter.

2. The sample probe of claim 1, the deflector substantially covering the sample probe tip filter.

3. The sample probe of claim 1, further comprising at least one pipe section that encloses at least a portion of the sample probe tip filter.

4. The sample probe of claim 3, the at least one pipe section comprising one or more concentric pipe sections.

5. The sample probe of claim 3, the at least one pipe section having at least one opening formed therein to allow gases to exit the at least one opening and to prevent the gases from traveling along the deflector to the sample probe tip filter.

6. The sample probe of claim 1, the deflector connected directly or indirectly to the support sleeve pipe.

7. The sample probe of claim 1, a portion of the sample probe tip filter disposed outside of the support sleeve pipe.

8. The sample probe of claim 1, the deflector extending beyond an end of the support sleeve pipe to substantially cover the sample probe tip filter.

9. The sample probe of claim 1, the deflector being connected to the support sleeve pipe such that the deflector is located upstream of the sample probe tip filter when the sample probe is placed in a gas sampling stream.

10. A sample probe for sampling flue gas in a gas sampling stream, comprising:
    a sample probe filter having a tip portion located at one end of the sample probe filter, the tip portion of the sample probe filter being operable to sample the flue gas in the gas sampling stream;
    a deflector disposed in relation to the sample probe filter, the deflector having a length that at least substantially covers the sample probe filter; and
    a support sleeve pipe, a portion of the sample probe filter being disposed within the support sleeve pipe, and the support sleeve pipe being configured for providing support to the sample probe filter to substantially avoid bending of the sample probe filter.

11. The sample probe of claim 10, the deflector being located upstream of the sample probe filter when the sample probe is placed in the gas sampling stream.

12. The sample probe of claim 10, the deflector being connected directly or indirectly to the support sleeve pipe.

13. The sample probe of claim 10, the sample probe filter comprising at least one pipe section that encloses at least a portion of the sample probe filter.

14. The sample probe of claim 13, the at least one pipe section having at least one opening formed therein to prevent gases exiting the at least one pipe section from traveling along the deflector to the sample probe filter.

15. The sample probe of claim 10, the deflector substantially covering the support sleeve pipe, the support sleeve pipe having at least one opening formed therein to allow gases to exit the opening and prevent the exiting gases from traveling along the deflector to the sample probe tip filter.

16. A sample probe, comprising:
    a sample probe tip filter;
    a deflector that connects to a support sleeve pipe, the deflector having a length that extends beyond an end of the support sleeve pipe, and a portion of the sample probe tip filter being disposed within the support sleeve pipe, the support sleeve pipe being configured for providing support to the sample probe tip filter to substantially avoid bending of the sample probe tip filter.

17. The sample probe of claim 16, the deflector being located upstream of the support sleeve pipe when the sample probe extension is placed in a gas sampling stream.

18. The sample probe of claim 16, the deflector comprising a partial section of an extension of the support sleeve pipe, the partial section being located upstream of the support sleeve pipe when the sample probe extension is placed in a gas sampling stream, the deflector having at least one opening formed therein to prevent exiting gases from traveling along the deflector.

* * * * *